United States Patent [19]

Yamamoto et al.

[11] 4,079,053

[45] * Mar. 14, 1978

[54] BENZODIAZEPINE DERIVATIVES

[75] Inventors: Hisao Yamamoto, Nishinomiya; Shigeho Inaba, Takarazuka; Toshiyuki Hirohashi, Ashiya; Michihiro Yamamoto, Toyonaka; Kikuo Ishizumi; Mitsuhiro Akatsu, both of Ikeda; Isamu Maruyama, Minoo; Kazuo Mori, Kobe; Yoshiharu Kume; Takahiro Izumi, both of Takarazuka, all of Japan

[73] Assignee: Sumitomo Chemical Company, Limited, Osaka, Japan

[*] Notice: The portion of the term of this patent subsequent to Mar. 1, 1994, has been disclaimed.

[21] Appl. No.: 710,665

[22] Filed: Aug. 2, 1976

Related U.S. Application Data

[63] Continuation of Ser. No. 497,936, Aug. 16, 1974, Pat. No. 4,010,154, which is a continuation of Ser. No. 111,141, Jan. 29, 1971, Pat. No. 3,867,372.

[30] Foreign Application Priority Data

| Feb. 3, 1970 | Japan | 45-9691 |
| Mar. 5, 1970 | Japan | 45-10533 |
| Jun. 24, 1970 | Japan | 45-55529 |
| Jun. 24, 1970 | Japan | 45-55530 |

[51] Int. Cl.$^2$ .................................... C07D 243/24
[52] U.S. Cl. .......................... 260/239.3 D; 424/244; 424/263
[58] Field of Search ............... 260/239.3 D; 424/244

[56] References Cited

U.S. PATENT DOCUMENTS

| 3,784,542 | 1/1974 | Hellerbach et al. | 260/239.3 D |
| 4,010,154 | 3/1977 | Yamamoto et al. | 260/239.3 D |

OTHER PUBLICATIONS

Sternbach, et al., Some Aspects of Structure–Activity Relationship in Psychotropic Agents of the 1,4-Benzodiazepine Series CSIR New Delhi, India, (1966).

Primary Examiner—Natalie Trousof
Assistant Examiner—Robert T. Bond
Attorney, Agent, or Firm—Farrell R. Werbow

[57] ABSTRACT

Novel 1-substituted benzodiazepine derivatives and salt thereof having the formula,

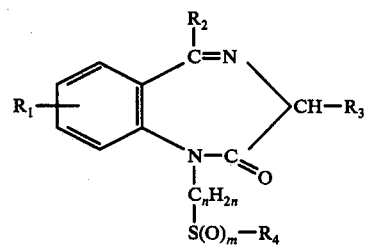

wherein $R_1$ is a hydrogen atom, a halogen atom, a nitro group, a cyano group, a lower alkoxy group or a trifluoromethyl group; $R_2$ is a pyridyl group or a group of the formula

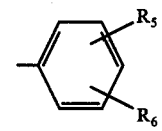

wherein $R_5$ and $R_6$ represent individually a hydrogen atom, a halogen atom, a lower alkyl group or a trifluoromethyl group); $R_3$ is a hydrogen atom or a lower alkyl group; $R_4$ is a lower alkyl, cycloalkyl, cycloalkylalkyl, aryl or aralkyl group; $m$ is 1 or 2; and $n$ is an integer of 1 to 4, and a process for preparation thereof and pharmaceutical use of the same.

The benzodiazepine derivatives are effective as tranquillizers, muscle-relaxants and hypnotics.

3 Claims, No Drawings

BENZODIAZEPINE DERIVATIVES

This is a continuation of application Ser. No. 497,936 filed Aug. 16, 1974, now U.S. Pat. No. 4,010,154, which in turn is a continuation of U.S. Ser. No. 111,141, filed Jan. 29, 1971, now U.S. Pat. No. 3,867,372.

This invention relates to novel 1-substituted benzodiazepine derivatives and salts thereof. More particularly, the invention pertains to novel 1-substituted benzodiazepine derivatives, and salts thereof, represented by the general formula (I).

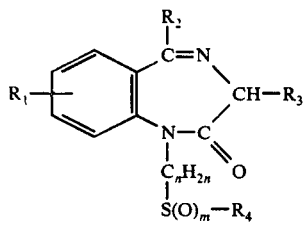

wherein $R_1$ is a hydrogen atom, a halogen atom, a nitro group, a cyano group, a lower $C_1$-$C_4$ alkoxy group or a trifluoromethyl group; $R_2$ is a pyridyl group, or a group of the formula

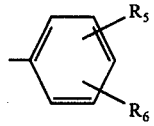

(where $R_5$ and $R_6$ represent individually a hydrogen atom, a halogen atom, a lower $C_1$-$C_2$ alkyl group or a trifluoromethyl group); $R_3$ is a hydrogen atom or a lower $C_1$-$C_4$ alkyl group; $R_4$ is a lower $C_1$-$C_4$ alkyl group, a $C_3$-$C_6$ cycloalkkyl group, a $C_3$-$C_6$ cycloalkyl-$C_1$-$C_4$ alkyl group, an aryl group or an aralkyl group, and $m$ is 1 or 2; and $n$ is an integer of 1 to 4, and a process for preparation thereof nd pharmaceutical use of the same.

In the compounds represented by the aforesaid general formula (I), the halogen atom includes fluorine, chlorine, bromine and iodine; the alkyl group includes straight-chain and branched-chain alkyl groups; the lower alkyl group includes, for example, methyl, ethyl, n-propyl, iso-propyl, n-butyl and t-butyl groups; the lower alkoxy group includes, for example, methoxy, ethoxy, n-propoxy, iso-propoxy, n-butoxy and t-butoxy groups; the cycloalkyl group includes, for example, cyclopropyl, cyclobutyl, cyclohexyl and cyclopentyl groups; the cycloalkylalkyl group includes, for example, cyclopropylmethyl, cyclobutylmethyl, cyclobutylethyl, cyclopentylmethyl, cyclohexyl methyl and cyclohexylethyl groups; the aryl group includes, for example, phenyl and mono- or disubstituted phenyl groups wherein the substituents in the phenyl ring can be halogen atoms such as chlorine, fluorine, bromine or iodine, lower alkyl such as methyl or ethyl, lower alkoxy such as methoxy or ethoxy; nitro and trifluoromethyl; and the aralkyl group includes, for example, benzyl and phenethyl groups; and the alkylene group of the formula —$C_nH_{2n}$— represents a straight-chain or branched-chain alkylene group having 1 to 4 carbon atoms and includes, for example, methylene, ethylene, 1-methylethylene, 2-methylethylene, trimethylene, 1-methyltrimethylene and 2-methyltrimethylene groups.

The 1-substituted benziodazepine derivatives represented by the aforesaid general formula (I) and salts thereof are novel compounds. It has surprisingly been found by the present inventors that the compounds represented by the formula (I), especially the compounds represented by the formula,

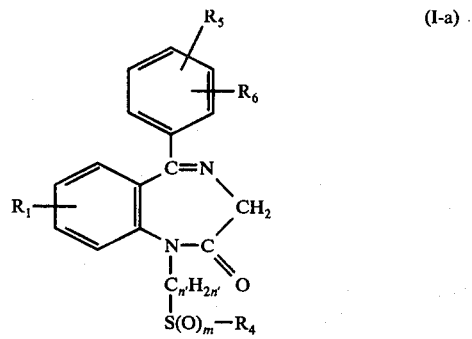

wherein $R_1$, $R_4$, $R_5$, $R_6$ and $m$ are as defined in the formula (I) above, and $n'$ represents 2 or 3, and their pharmaceutically acceptable salts with inorganic and organic acids, have valuable pharmacological properties, in particular excellent tranquillizing, sedative, muscle relaxant, spasmolytic and hypnotic activities.

Accordingly, an object of the present invention is to provide novel and useful benzodiazepines and salts thereof which have excellent pharmacological properties. Another object is to provide a process for producing such novel and useful benzodiazepines and salts thereof. A further object is to provide pharmaceutical composition containing such novel and useful benzodiazepines or salts thereof. Other objects and merits of the present invention will be apparent from the following descriptions.

In order to accomplish these objects the present invention provides novel benzodiazepines represented by the formula (I) and acid addition salts thereof.

According to the present invention, the novel benzodiazepines represented by the formula (I) may be prepared by a variety of methods.

One method for producing the benzodiazepines of the formula (I) which comprises reacting 1-unsubstituted benzodiazepines represented by the formula

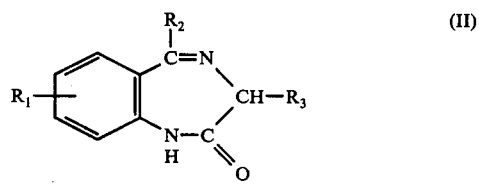

wherein $R_1$, $R_2$ and $R_3$ are as defined in the formula (I) above, with a reactive ester of a compound represented by the formula,

wherein $R_4$, $m$ and $n$ are as defined above. Examples of reactive esters include hydrohalic acid esters such as the chlorides, bromides and iodides and sulfonic acid esters such as methanesulfonate, p-toluenesulfonate, β-naphthalenesulfonate and trichloromethansulfonate. The reaction may be carried out by reacting a compound of the formula (II) with a reactive ester of the compound of the formula (III) in the presence of an alkaline agent or by contacting the compound of the formula (II) with an alkaline agent to form the metal salt and then contacting the resulting metal salt with a reactive ester of the compound of the formula (III). Examples of the alkaline agents include alkali metal hydride such as sodium hydride or lithium hydride, alkali metal hydroxide such as potassium hydroxide, alkali metal amide such as sodium amide, potassium amide or lithium amide, alkylalkali such as butyl lithium, phenylalkali such as phenyl lithium, alkali metal alcoholate such as sodium methylate, sodium ethylate, potassium tertiarybutoxide or the like. The reaction may generally be effected in an organic solvent or solvent mixture. Suitable solvents include benzene, toluene, xylene, dimethylformamide, dimethylacetamide, diphenyl ether, diglyme, dimethyl sulfoxide, methyl ethyl ketone, N-methyl pyrrolidone and the like, and a solvent mixture thereof. The reactin may be carried out at a temperature within the range between about room temperature and the boiling point of the solvent employed.

Another method for preparing benzodiazepines of the formula (I) which comprises treating an aminophenyl ketone derivative represented by the formula,

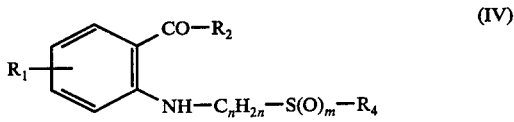

wherein $R_1$, $R_2$, $R_4$, $n$ and $m$ are as defined in the formula (I) above, with a 2,5-oxazolidinedione having the formula,

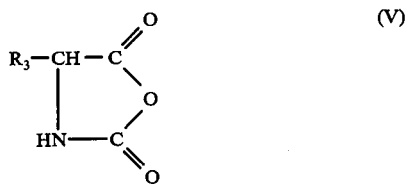

wherein $R_3$ is as defined in the formula (I) above. The reaction is carried out in the presence of a solvent or solvent mixture. Suitable solvent include, for example, chloroform, carbon tetrachloride, methylene chloride, ethylene chloride, ether, diisopropyl ether, tetrahydrofuran, dioxane, water, methanol, ethanol, dimethylformamide, dimethyl sulfoxide or a mixture thereof. The reaction is, generally, carried out in the presence of an acid. The acid used in this process includes hydrogen chloride, hydrogen bromide, sulfuric acid, phosphoric acid, polyphosphoric acids, borontrifluoride and para-toluenesulfonic acid. The reaction is effected at a temperature ranging from −25° C to about 120° C, and more preferably from about 0° C to about 30° C. Temperatures above and below the aforesaid ranges can also be employed but are less preferred. In most instances, the reaction can be conducted at room temperature or below. Pressure is not critical and the process can be conducted at atmospheric, subatmospheric or superatmospheric pressure. The process, if desired, can be conducted in an inert atmosphere, such as nitrogen, argon and the like.

Although the mole ratio of the 2,5-dione derivative to the aminophenyl ketone derivative is not critical, it is preferable to use at least stoichiometric amount of the reaction. In most cases, it is more preferable to use an excess of the -2,5-dione derivative.

The reactant can be, if necessary, heated in a suitable solvent, such as dimethylsulfoxide, dimethylformamide or the like to complete the reaction.

Yet another method for preparing benzodiazepine derivative of the formula (I) which comprises treating an 2-aminomethylindole derivative, or an acid addition salt thereof, having the formula,

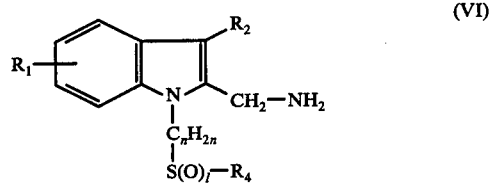

wherein $R_1$, $R_2$, $R_4$ and $n$ are as defined in the formula (I) above, and l represents 0, 1 or 2, with an oxidizing agent. Examples of the acid addition salt include hydrochloride, hydrobromide, sulfate or phosphate. The oxidizing agent for this process includes, for example, ozone, hydrogen, peroxide, peracid (e.g. performic, peracetic and perbenzoic acid), chromic acid and potassium permanganate, but is not limited to the named compounds. Generally the reaction progresses readily at room temperature, but the temperature may be higher or lower, for example, 0°–about 100° C or a boiling point of the solvents, preferably 10° – 60° C, as necessary to effect the desired control of the reaction, and the reaction temperature varies depending on the oxidizing agent employed. The preferable oxidizing agent is chromic acid or ozone. The reaction is preferably effected in the presence of a solvent. The choice of solvent depends on the oxidizing agent employed, and is selected from the group consisting of water, acetone, carbon tetrachloride, formic acid, acetic acid, sulfuric acid and the like. The oxidizing agent is used in the stoichiometric amount or more.

Where the oxidation is carried out by use of chromic acid in the presence of acetic acid, it is preferable that the chromic acid may be used in 2 – 3 times the equimolar amount and the reaction may be carried out at room temperature. A 2-aminomethylindole derivative is dissolved or suspended in the solvent and the oxidizing agent is added to the solution or suspension with stirring.

Where the oxidation is carried out by use of ozone, the reaction is preferably carried out at room temperature. A 2-aminomethylindole derivative is dissolved or suspended in the solvent such as formic acid, acetic acid, carbon tetrachloride or the like and ozonized oxygen is bubbled into the solution or suspension with stirring.

The desired benzodiazepine derivative can be separated from the reaction mixture in a crude form by extraction, with or without prior neutralization, and by evaporation to dryness. The product is further purified, if desired, by recrystallization from a suitable solvent such as ethanol, isopropanol, isopropylether or their mixture or the like in a standard procedure.

Still another method for preparing benzodiazepine derivative of the formula (I-a) which comprises contacting benzodiazepine derivative or salt thereof having the formula,

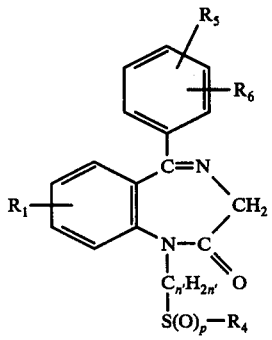

(VII)

wherein $R_1$, $R_4$, $R_5$, $R_6$ and $n'$ are as defined in the formula (I-a) above, and $p$ is zero or 1; with an oxidizing agent. As the oxidizing agent, there is used, for example, chromic acid, nitric acid, hydrogen peroxide, organic peracid (e.g. performic, peracetic, perbenzoic or m-chloroperbenzoic acid), sodium periodate, potassium periodate persulfate, selenium dioxide, lead tetracetate, manganese dioxide or ruthenium tetraoxide. The reaction is advantageously effected in the presence of a solvent, in general. The choice of the solvent depends on the oxidizing agent employed, and is selected from the group consisting of water, chloroform, carbon tetrachloride, acetone, acetic acid, formic acid, sulfuric acid, pyridine, dioxane, benzene, toluene, ether, ethyl acetate, methanol, ethanol and the like, and a mixture thereof. The reaction temperature varies depending on the oxidizing agent employed. When it is desired to obtain a compound of the formula (I-a) wherein $m$ is 1, the reaction is advantageously effected at or below room temperature. When it is desired to obtain a compound of the formula (I-a) wherein $m$ is 2, the reaction is advantageously effected at or above room temperature.

The other method for preparing benzodiazepine of the formula (I-a) which comprises treating compound represented by the formula,

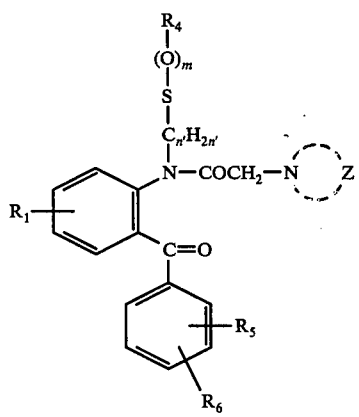

(VIII)

wherein $R_1$, $R_4$, $R_5$, $R_6$, $m$ and $n'$ are as defined in the formula (I) and (I-a) above and Z is a nitrogen protecting system comprising at least one readily removable group, whereby to remove the system Z. Said protecting system Z is comprised of a group or groups which can be readily removed by conventional procedures well disclosed in the literature. Examples of the protecting system Z are a phthaloyl group, a lower alkylidene group such as isopropylidene, a benzal group, one carbobenzoxy group and one hydrogen that is,

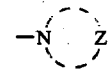

is a group of the formula,

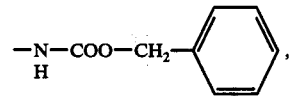

and the like. The removal of the protecting system is effected by utilizing conventional procedures well established in the art. For example, if Z in the formula (VIII) represents a phthaloyl group as the protective group, the system is removed by reacting such compounds with hydrazine derivatives such as hydrazine hydrate or phenylhydrazine, whereby to prepare the objective compound of the formula (I-a). The reaction is preferably effected in the presence of a solvent or solvent mixture. Suitable solvents are, for example, methanol, ethanol, isopropanol, water and the mixture thereof. The reaction is carried out at a temperature within the range between about room temperature and the boiling point of the solvent employed.

If the system Z in the formula (VIII) consists of a carbobenzoxy group as the removable group and hydrogen, the removal of the system is effected by using hydrogen halide. Suitable hydrogen halides include hydrogen bromide and hydrogen chloride. The preferred hydrogen halide is hydrogen bromide. Hydrohalic acid such as hydrobromic acid and hydrochloric acid may be used as the hydrogen halide. The reaction is carried out in a solvent or solvent mixture. Suitable solvents are methanol, ethanol, acetic acid, water or the like, or a mixture thereof.

The reaction is carried out at a temperature within the range between about room temperature and the boiling point of the solvent used. The process may ether proceed directly to the desired compounds of the formula (I-a) or through intermediates of the formula,

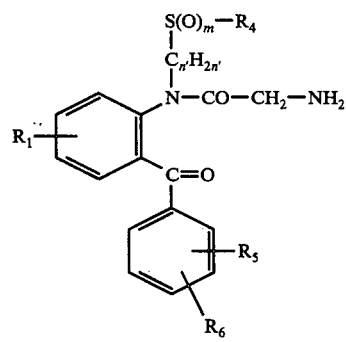

(IX)

wherein $R_1$, $R_4$, $R_5$, $R_6$, $m$ and $n'$ are as defined above, which may then be cyclized to the desired compound of the formula (I-a). The intermediate of the formula (IX), if desired, may be isolated as the hydrohalides by the selection of mild reaction conditions, such as appropriate reaction temperature and reaction time. The compound of the formula (IX) may be ring-closed to the desired compound of the formula (I-a) by being allowed to stand at room temperature or at an elevated temperature in a suitable solvent such as acetic acid, methanol, ethanol, pyridine, dimethyl sulfoxide or the like with or without treatment with a base.

According to the process of the present invention, there are obtained, for example, the following compounds:

1-Methylsulfonylmethyl-5-phenyl-7-chloro-1,3-dihydro-2H-1,4-benzodiazepin-2-one
1-Methylsulfonylmethyl-5-phenyl-7-nitro-1,3-dihydro-2H-1,4-benzodiazepin-2-one
1-Methylsulfonylmethyl-5-(o-fluorophenyl)-7-chloro-1,3-dihydro-2H-1,4-benzodiazepin-2-one
1-Methylsulfonylmethyl-5-(2'-pyridyl)-7-bromo-1,3-dihydro-2H-1,4-benzodiazepin-2-one
1-Ethylsulfonylmethyl-5-phenyl-7-chloro-1,3-dihydro-2H-1,4-benzodiazepin-2-one
1-Ethylsulfonylmethyl-5-phenyl-7-nitro-1,3-dihydro-2H-1,4-benzodiazepin-2-one
1-Ethylsulfonylmethyl-5-(o-fluorophenyl)-7-chloro-1,3-dihydro-2H-1,4-benzodiazepin-2-one
1-Ethylsulfonylmethyl-5-(2'-pyridyl)-7-bromo-1,3-dihydro-2H-1,4-benzodiazepin-2-one
1-Propylsulfonylmethyl-5-(o-fluorophenyl)-7-chloro-1,3-dihydro-2H-1,4-benzodiazepin-2-one
1-Methylsulfonylmethyl-5-phenyl-7-methoxy-1,3-dihydro-2H-1,4-benzodiazepin-2-one
1-Methylsulfonylmethyl-5-phenyl-7-trifluoromethyl-1,3-dihydro-2H-1,4-benzodiazepin-2-one
1-Methylsulfonylmethyl-5-phenyl-1,3-dihydro-2H-1,4-benzodiazepin-2-one
1-Methylsulfonylmethyl-3-methyl-5-phenyl-7-chloro-1,3-dihydro-2H-1,4-benzodiazepin-2-one
1-Methylsulfonylmethyl-5-(2'-pyridyl)-7-chloro-1,3-dihydro-2H-1,4-benzodiazepin-2-one
1-Methylsulfonylmethyl-5-(o-chlorophenyl)-7-chloro-1,3-dihydro-2H-1,4-benzodiazepin-2-one
1-Methylsulfonylmethyl-5-(o-tolyl)-7-chloro-1,3-dihydro-2H-1,4-benzodiazepin-2-one
1-Methylsulfonylmethyl-5-(o-chlorophenyl)-7-nitro-1,3-dihydro-2H-1,4-benzodiazepin-2-one
1-Methylsulfonylmethyl-5-(o-trifluoromethylphenyl)-7-chloro-1,3-dihydro-2H-1,4-benzodiazepin-2-one
1-Ethylsulfonylmethyl-5-phenyl-7-cyano-1,3-dihydro-2H-1,4-benzodiazepin-2-one
1-Ethylsulfonylmethyl-5-phenyl-7-nitro-1,3-dihydro-2H-1,4-benzodiazepin-2-one
1-Ethylsulfonylmethyl-5-phenyl-7-methoxy-1,3-dihydro-2H-1,4-benzodiazepin-2-one
1-Ethylsulfonylmethyl-5-phenyl-7-trifluoromethyl-1,3-dihydro-2H-1,4-benzodiazepin-2-one
1-Ethylsulfonylmethyl-5-phenyl-7-bromo-1,3-dihydro-2H-1,4-benzodiazepin-2-one
1-Ethylsulfonylmethyl-5-phenyl-1,3-dihydro-2H-1,4-benzodiazepin-2-one
1-Ethylsulfonylmethyl-3-methyl-5-phenyl-7-chloro-1,3-dihydro-2H-1,4-benzodiazepin-2-one
1-Ethylsulfonylmethyl-5-(2'-pyridyl)-7-chloro-1,3-dihydro-2H-1,4-benzodiazepin-2-one
1-Ethylsulfonylmethyl-5-(o-chlorophenyl)-7-chloro-1,3-dihydro-2H-1,4-benzodiazepin-2-one
1-Ethylsulfonylmethyl-5-(o-tolyl)-7-chloro-1,3-dihydro-2H-1,4-benzodiazepin-2-one
1-Ethylsulfonylmethyl-5-(o-chlorophenyl)-7-nitro-1,3-dihydro-2H-1,4-benzodiazepin-2-one
1-Ethylsulfonylmethyl-5-(o-trifluoromethylphenyl)-7-chloro-1,3-dihydro-2H-1,4-benzodiazepin-2-one
1-Propylsulfonylmethyl-5-phenyl-7-chloro-1,3-dihydro-2H-1,4-benzodiazepin-2-one
1-Propylsulfonylmethyl-5-(o-chlorophenyl)-7-chloro-1,3-dihydro-2H-1,4-benzodiazepin-2-one
1-Propylsulfonylmethyl-5-(o-tolyl)-7-chloro-1,3-dihydro-2H-1,4-benzodiazepin-2-one
1-Propylsulfonylmethyl-5-(o-chlorophenyl)-7-nitro-1,3-dihydro-2H-1,4-benzodiazepin-2-one
1-Propylsulfonylmethyl-5-(o-trifluoromethylphenyl)-7-chloro-1,3-dihydro-2H-1,4-benzodiazepin-2-one
1-(β-Methylsulfonylethyl)-5-phenyl-7-chloro-1,3-dihydro-2H-1,4-benzodiazepin-2-one
1-(β-Methylsulfonylethyl)-5-phenyl-7-cyano-1,3-dihydro-2H-1,4-benzodiazepin-2-one
1-(β-Methylsulfonylethyl)-5-phenyl-7-nitro-1,3-dihydro-2H-1,4-benzodiazepin-2-one
1-(β-Methylsulfonylethyl)-5-phenyl-7-methoxy-1,3-dihydro-2H-1,4-benzodiazepin-2-one
1-(β-Methylsulfonylethyl)-5-phenyl-7-trifluoromethyl-1,3-dihydro-2H-1,4-benzodiazepin-2-one
1-(β-Methylsulfonylethyl)-5-phenyl-7-bromo-1,3-dihydro-2H-1,4-benzodiazepin-2-one
1-(β-Methylsulfonylethyl)-5-phenyl-1,3-dihydro-2H-1,4-benzodiazepin-2-one
1-(β-Methylsulfonylethyl)-3-methyl-5-phenyl-7-chloro-1,3-dihydro-2H-1,4-benzodiazepin-2-one
1-(β-Methylsulfonylethyl)-5-(2'-pyridyl)-7-chloro-1,3-dihydro-2H-1,4-benzodiazepin-2-one
1-(β-Methylsulfonylethyl)-5-(o-fluorophenyl)-7-chloro-1,3-dihydro-2H-1,4-benzodiazepin-2-one
1-(β-Methylsulfonylethyl)-5-(2'-pyridyl)-7-bromo-1,3-dihydro-2H-1,4-benzodiazepin-2-one
1-(β-Methylsulfonylethyl)-5-(o-chlorophenyl)-7-chloro-1,3-dihydro-2H-1,4-benzodiazepin-2-one
1-(β-Methylsulfonylethyl)-5-(o-tolyl)-7-chloro-1,3-dihydro-2H-1,4-benzodiazepin-2-one
1-(β-Methylsulfonylethyl)-5-(o-chlorophenyl)-7-nitro-1,3-dihydro-2H-1,4-benzodiazepin-2-one
1-(β-Methylsulfonylethyl)-5-(o-trifluoromethylphenyl)-7-chloro-1,3-dihydro-2H-1,4-benzodiazepin-2-one
1-(β-Ethylsulfonylethyl)-5-phenyl-7-chloro-1,3-dihydro-2H-1,4-benzodiazepin-2-one
1-(β-Ethylsulfonylethyl)-5-phenyl-7-cyano-1,3-dihydro-2H-1,4-benzodiazepin-2-one
1-(β-Ethylsulfonylethyl)-5-phenyl-7-nitro-1,3-dihydro-2H-1,4-benzodiazepin-2-one
1-(β-Ethylsulfonylethyl)-5-phenyl-7-trifluoromethyl-1,3-dihydro-2H-1,4-benzodiazepin-2-one
1-(β-Ethylsulfonylethyl)-5-phenyl-7-bromo-1,3-dihydro-2H-1,4-benzodiazepin-2-one
1-(β-Ethylsulfonylethyl)-5-(o-fluorophenyl)-7-chloro-1,3-dihydro-2H-1,4-benzodiazepin-2-one
1-(β-Ethylsulfonylethyl)-5-(2'-pyridyl)-7-bromo-1,3-dihydro-2H-1,4-benzodiazepin-2-one
1-(β-Ethylsulfonylethyl)-5-(o-chlorophenyl)-7-chloro-1,3-dihydro-2H-1,4-benzodiazepin-2-one
1-(β-Ethylsulfonylethyl)-5-(o-tolyl)-7-chloro-1,3-dihydro-2H-1,4-benzodiazepin-2-one
1-(β-Ethylsulfonylethyl)-5-(o-chlorophenyl)-7-nitro-1,3-dihydro-2H-1,4-benzodiazepin-2-one
1-(β-Propylsulfonylethyl)-5-phenyl-7-chloro-1,3-dihydro-2H-1,4-benzodiazepin-2-one
1-(β-Propylsulfonylethyl)-5-phenyl-7-nitro-1,3-dihydro-2H-1,4-benzodiazepin-2-one
1-(β-Isopropylsulfonylethyl)-5-(o-chlorophenyl)-7-chloro-1,3-dihydro-2H-1,4-benzodiazepin-2-one
1-(β-Isopropylsulfonylethyl)-5-(o-tolyl)-7-chloro-1,3-dihydro-2H-1,4-benzodiazepin-2-one
1-(β-Isopropylsulfonylethyl)-5-(o-chlorophenyl)-7-nitro-1,3-dihydro-2H-1,4-benzodiazepin-2-one 1-(γ-Methylsulfonylpropyl)-5-phenyl-7-chloro-1,3-dihydro-2H-1,4-benzodiazepin-2-one
1-(γ-Methylsulfonylpropyl)-5-phenyl-7-nitro-1,3-dihydro-2H-1,4-benzodiazepin-2-one
1-(γ-Methylsulfonylpropyl)-5-(o-fluorophenyl)-7-chloro-1,3-dihydro-2H-1,4-benzodiazepin-2-one
1-(γ-Methylsulfonylpropyl)-5-(o-chlorophenyl)-7-chloro-1,3-dihydro-2H-1,4-benzodiazepin-2-one
1-(γ-Methylsulfonylpropyl)-5-(o-tolyl)-7-chloro-1,3-dihydro-2H-1,4-benzodiazepin-2-one
1-(γ-Methylsulfonylpropyl)-5-(o-chlorophenyl)-7-nitro-1,3-dihydro-2H-1,4-benzodiazepin-2-one
1-(γ-Ethylsulfonylpropyl)-5-phenyl-7-chloro-1,3-dihydro-2H-1,4-benzodiazepin-2-one
1-(γ-Ethylsulfonylpropyl)-5-phenyl-7-nitro-1,3-dihydro-2H-1,4-benzodiazepin-2-one
1-(γ-Ethylsulfonylpropyl)-5-phenyl-7-trifluoromethyl-1,3-dihydro-2H-1,4-benzodiazepin-2-one
1-(γ-Ethylsulfonylpropyl)-5-phenyl-7-bromo-1,3-dihydro-2H-1,4-benzodiazepin-2-one
1-(γ-Ethylsulfonylpropyl)-5-(2'-pyridyl)-7-chloro-1,3-dihydro-2H-1,4-benzodiazepin-2-one
1-(γ-Ethylsulfonylpropyl)-5-(o-fluorophenyl)-7-chloro-1,3-dihydro-2H-1,4-benzodiazepin-2-one
1-(γ-Ethylsulfonylpropyl)-5-(2'-pyridyl)-7-bromo-1,3-dihydro-2H-1,4-benzodiazepin-2-one
1-(γ-Ethylsulfonylpropyl)-5-(o-chlorophenyl)-7-chloro-1,3-dihydro-2H-1,4-benzodiazepin-2-one
1-(γ-Ethylsulfonylpropyl)-5-(o-tolyl)-7-chloro-1,3-dihydro-2H-1,4-benzodiazepin-2-one
1-(γ-Ethylsulfonylpropyl)-5-(o-chlorophenyl)-7-nitro-1,3-dihydro-2H-1,4-benzodiazepin-2-one
1-(γ-Ethylsulfonylpropyl)-5-(o-trifluoromethylphenyl)-7-chloro-1,3-dihydro-2H-1,4-benzodiazepin-2-one
1-Methylsulfinylmethyl-5-phenyl-7-chloro-1,3-dihydro-2H-1,4-benzodiazepin-2-one
1-Methylsulfinylmethyl-5-phenyl-7-cyano-1,3-dihydro-2H-1,4-benzodiazepin-2-one
1-Methylsulfinylmethyl-5-phenyl-7-nitro-1,3-dihydro-2H-1,4-benzodiazepin-2-one
1-Methylsulfinylmethyl-5-phenyl-7-methoxy-1,3-dihydro-2H-1,4-benzodiazepin-2-one
1-Methylsulfinylmethyl-5-phenyl-7-trifluoromethyl-1,3-dihydro-2H-1,4-benzodiazepin-2-one
1-Methylsulfinylmethyl-5-phenyl-7-bromo-1,3-dihydro-2H-1,4-benzodiazepin-2-one
1-Methylsulfinylmethyl-5-(2'-pyridyl)-7-chloro-1,3-dihydro-2H,1,4-benzodiazepin-2-one
1-Methylsulfinylmethyl-5-(o-fluorophenyl)-7-chloro-1,3-dihydro-2H-1,4-benzodiazepin-2-one
1-Methylsulfinylmethyl-5-(2'-pyridyl)-7-bromo-1,3-dihydro-2H-1,4-benzodiazepin-2-one
1-Methylsulfinylmethyl-5-(o-chlorophenyl)-7-chloro-1,3-dihydro-2H-1,4-benzodiazepin-2-one
1-Methylsulfinylmethyl-5-(o-tolyl)-7-chloro-1,3-dihydro-2H-1,4-benzodiazepin-2-one
1-Methylsulfinylmethyl-5-(o-chlorophenyl)-7-nitro-1,3-dihydro-2H-1,4-benzodiazepin-2-one
1-Ethylsulfinylmethyl-5-phenyl-7-chloro-1,3-dihydro-2H-1,4-benzodiazepin-2-one
1-Ethylsulfinylmethyl-5-phenyl-7-cyano-1,3-dihydro-2H-1,4-benzodiazepin-2-one
1-Ethylsulfinylmethyl-5-phenyl-7-nitro-1,3-dihydro-2H-1,4-benzodiazepin-2-one
1-Ethylsulfinylmethyl-5-phenyl-7-trifluoromethyl-1,3-dihydro-2H-1,4-benzodiazepin-2-one
1-Ethylsulfinylmethyl-5-phenyl-7-bromo-1,3-dihydro-2H-1,4-benzodiazepin-2-one
1-Ethylsulfinylmethyl-3-methyl-5-phenyl-7-chloro-1,3-dihydro-2H-1,4-benzodiazepin-2-one
1-Ethylsulfinylmethyl-5-(2'-pyridyl)-7-chloro-1,3-dihydro-2H-1,4-benzodiazepin-2-one
1-Ethylsulfinylmethyl-5-(o-fluorophenyl)-7-chloro-1,3-dihydro-2H-1,4-benzodiazepin-2-one
1-Ethylsulfinylmethyl-5-(2'-pyridyl)-7-bromo-1,3-dihydro-2H-1,4-benzodiazepin-2-one
1-Ethylsulfinylmethyl-5-(o-chlorophenyl)-7-chloro-1,3-dihydro-2H-1,4-benzodiazepin-2-one
1-Ethylsulfinylmethyl-5-(o-tolyl)-7-chloro-1,3-dihydro-2H-1,4-benzodiazepin-2-one
1-Ethylsulfinylmethyl-5-(o-chlorophenyl)-7-nitro-1,3-dihydro-2H-1,4-benzodiazepin-2-one
1-Ethylsulfinylmethyl-5-(o-trifluoromethylphenyl)-7-chloro-1,3-dihydro-2H-1,4-benzodiazepin-2-one
1-Propylsulfinylmethyl-5-phenyl-7-chloro-1,3-dihydro-2H-1,4-benzodiazepin-2-one
1-Propylsulfinylmethyl-5-phenyl-7-nitro-1,3-dihydro-2H-1,4-benzodiazepin-2-one
1-Isopropylsulfinylmethyl-5-phenyl-7-chloro-1,3-dihydro-2H-1,4-benzodiazepin-2-one
1-Isopropylsulfinylmethyl-5-(o-fluorophenyl)-7-chloro-1,3-dihydro-2H-1,4-benzodiazepin-2-one
1-Propylsulfinylmethyl-5-(o-chlorophenyl)-7-chloro-1,3-dihydro-2H-1,4-benzodiazepin-2-one
1-Propylsulfinylmethyl-5-(o-tolyl)-7-chloro-1,3-dihydro-2H-1,4-benzodiazepin-2-one
1-Propylsulfinylmethyl-5-(o-chlorophenyl)-7-nitro-1,3-dihydro-2H-1,4-benzodiazepin-2-one
1-(β-Methylsulfinylethyl)-5-phenyl-7-chloro-1,3-dihydro-2H-1,4-benzodiazepin-2-one
1-(β-Methylsulfinylethyl)-5-phenyl-7-cyano-1,3-dihydro-2H-1,4-benzodiazepin-2-one
1-(β-Methylsulfinylethyl)-5-phenyl-7-nitro-1,3-dihydro-2H-1,4-benzodiazepin-2-one
1-(β-Methylsulfinylethyl)-5-phenyl-7-methoxy-1,3-dihydro-2H-1,4-benzodiazepin-2-one
1-(β-Methylsulfinylethyl)-5-phenyl-7-trifluoromethyl-1,3-dihydro-2H-1,4-benzodiazepin-2-one
1-(β-Methylsulfinylethyl)-5-phenyl-7-bromo-1,3-dihydro-2H-1,4-benzodiazepin-2-one
1-(β-Methylsulfinylethyl)-5-phenyl-1,3-dihydro-2H-1,4-benzodiazepin-2-one
1-(β-Methylsulfinylethyl)-5-(o-fluorophenyl)-7-chloro-1,3-dihydro-2H-1,4-benzodiazepin-2-one
1-(β-Methylsulfinylethyl)-5-(2'-pyridyl)-7-bromo-1,3-dihydro-2H-1,4-benzodiazepin-2-one
1-(β-Methylsulfinylethyl)-5-(o-chlorophenyl)-7-chloro-1,3-dihydro-2H-1,4-benzodiazepin-2-one
1-(β-Methylsulfinylethyl)-5-(o-tolyl)-7-chloro-1,3-dihydro-2H-1,4-benzodiazepin-2-one
1-(β-Methylsulfinylethyl)-5-(o-chlorophenyl)-7-nitro-1,3-dihydro-2H-1,4-benzodiazepin-2-one
1-(β-Methylsulfinylethyl)-5-(o-trifluoromethylphenyl)-7-chloro-1,3-dihydro-2H-1,4-benzodiazepin-2-one
1-(β-Ethylsulfinylethyl)-5-phenyl-7-chloro-1,3-dihydro-2H-1,4-benzodiazepin-2-one
1-(β-Ethylsulfinylethyl)-5-phenyl-7-cyano-1,3-dihydro-2H-1,4-benzodiazepin-2-one
1-(β-Ethylsulfinylethyl)-5-phenyl-7-nitro-1,3-dihydro-2H-1,4-benzodiazepin-2-one
1-(β-Ethylsulfinylethyl)-5-phenyl-7-trifluoromethyl-1-1,3-dihydro-2H-1,4-benzodiazepin-2-one
1-(β-Ethylsulfinylethyl)-5-phenyl-7-bromo-1,3-dihydro-2H-1,4-benzodiazepin-2-one 1-(β-Ethylsulfinylethyl)-5-(2'-pyridyl)-7-chloro-1,3-dihydro-2H-1,4-benzodiazepin-2-one 1-(β-Ethylsulfinylethyl)-5-(o-fluorophenyl)-7-chloro-1,3-dihydro-2H-1,4-benzodiazepin-2-one
1-(β-Ethylsulfinylethyl)-5-(2'-pyridyl)-7-bromo-1,3-dihydro-2H-1,4-benzodiazepin-2-one
1-(β-Ethylsulfinylethyl)-5-(o-chlorophenyl)-7-chloro-1,3-dihydro-2H-1,4-benzodiazepin-2-one
1-(β-Ethylsulfinylethyl)-5-(o-tolyl)-7-chloro-1,3-dihydro-2H-1,4-benzodiazepin-2-one
1-(β-Ethylsulfinylethyl)-5-(o-chlorophenyl)-7-nitro-1,3-dihydro-2H-1,4-benzodiazepin-2-one
1-(β-Ethylsulfinylethyl)-5-(o-trifluoromethylphenyl)-7-chloro-1,3-dihydro-2H-1,4-benzodiazepin-2-one
1-(β-Propylsulfinylethyl)-5-phenyl-7-chloro-1,3-dihydro-2H-1,4-benzodiazepin-2-one
1-(β-Propylsulfinylethyl)-5-phenyl-7-nitro-1,3-dihydro-2H-1,4-benzodiazepin-2-one
1-(β-Propylsulfinylethyl)-5-(o-fluorophenyl)-7-chloro-1,3-dihydro-2H-1,4-benzodiazepin-2-one
1-(β-Propylsulfinylethyl)-5-(o-chlorophenyl)-7-chloro-1,3-dihydro-2H-1,4-benzodiazepin-2-one
1-(β-Propylsulfinylethyl)-5-(o-tolyl)-7-chloro-1,3-dihydro-2H-1,4-benzodiazepin-2-one
1-(β-Propylsulfinylethyl)-5-(o-chlorophenyl)-7-nitro-1,3-dihydro-2H-1,4-benzodiazepin-2-one
1-(β-Isopropylsulfinylethyl)-5-(o-fluorophenyl)-7-chloro-1,3-dihydro-2H-1,4-benzodiazepin-2-one
1-(γ-Methylsulfinylpropyl)-5-phenyl-7-chloro-1,3-dihydro-2H-1,4-benzodiazepin-2-one
1-(γ-Methylsulfinylpropyl)-5-phenyl-7-nitro-1,3-dihydro-2H-1,4-benzodiazepin-2-one
1-(γ-Methylsulfinylpropyl)-5-phenyl-7-trifluoromethyl-1,3-dihydro-2H-1,4-benzodiazepin-2-one
1-(γ-Methylsulfinylpropyl)-5-phenyl-7-bromo-1,3-dihydro-2H-1,4-benzodiazepin-2-one
1-(γ-Methylsulfinylpropyl)-3-methyl-5-phenyl-7-chloro-1,3-dihydro-2H-1,4-benzodiazepin-2-one
1-(γ-Methylsulfinylpropyl)-5-(o-fluorophenyl)-7-chloro-1,3-dihydro-2H-1,4-benzodiazepin-2-one
1-(γ-Methylsulfinylpropyl)-5-(2'-pyridyl)-7-bromo-1,3-dihydro-2H-1,4-benzodiazepin-2-one
1-(γ-Methylsulfinylpropyl)-5-(o-chlorophenyl)-7-chloro-1,3-dihydro-2H-1,4-benzodiazepin-2-one
1-(γ-Methylsulfinylpropyl)-5-(o-tolyl)-7-chloro-1,3-dihydro-2H-1,4-benzodiazepin-2-one
1-(γ-Methylsulfinylpropyl)-5-(o-chlorophenyl)-7-nitro-1,3-dihydro-2H-1,4-benzodiazepin-2-one
1-(γ-Ethylsulfinylpropyl)-5-phenyl-7-chloro-1,3-dihydro-2H-1,4-benzodiazepin-2-one
1-(γ-Ethylsulfinylpropyl)-5-phenyl-7-nitro-1,3-dihydro-2H-1,4-benzodiazepin-2-one
1-(γ-Ethylsulfinylpropyl)-5-phenyl-7-trifluoromethyl-1,3-dihydro-2H-1,4-benzodiazepin-2-one
1-(γ-Ethylsulfinylpropyl)-5-phenyl-7bromo-1,3-dihydro-2H-1,4-benzodiazepin-2-one
1-(γ-Ethylsulfinylpropyl)-5-(o-fluorophenyl)-7-chloro-1,3-dihydro-2H-1,4-benzodiazepin-2-one
1-(γ-Ethylsulfinylpropyl)-5-(2'-pyridyl)-7-bromo-1,3-dihydro-2H-1,4-benzodiazepin-2-one
1-(γ-Ethylsulfinylpropyl)-5-(o-chlorophenyl)-7-chloro-1,3-dihydro-2H-1,4-benzodiazepin-2-one
1-(γ-Ethylsulfinylpropyl)-5-(o-tolyl)-7-chloro-1,3-dihydro-2H-1,4-benzodiazepin-2one
1-(γ-Ethylsulfinylpropyl)-5-(o-chlorophenyl)-7-nitro-1,3-dihydro-2H-1,4-benzodiazepin-2-one
1-(γ-Ethylsulfinylpropyl)-5-(o-trifluoromethylphenyl)-7-chloro-1,3-dihydro-2H-1,4-benzodiazepin-2-one
1-Methylsulfonylmethyl-5-(o,o'-dichlorophenyl)-7-chloro-1,3-dihydro-2H-1,4-benzodiazepin-2-one
1-Methylsulfonylmethyl-5-(o-fluoro-o'-chlorophenyl)-7-chloro-1,3-dihydro-2H-1,4-benzodiazepin-2one
1-Ethylsulfonylmethyl-5-(o,o'-difluorophenyl)-7-chloro-1,3-dihydro-2H-1,4-benzodiazepin-2-one
1-Ethylsulfonylmethyl-5-(o,o'-dichlorophenyl)-7-chloro-1,3-dihydro-2H-1,4-benzodiazepin-2-one
1-Ethylsulfonylmethyl-5-(o,o'-xylyl)-7-chloro-1,3-dihydro-2H-1,4-benzodiazepin-2-one
1-Ethylsulfonylmethyl-5-(o-fluoro-p-chlorophenyl)-7-chloro-1,3-dihydro-2H-1,4-benzodiazepin-2-one
1-(β-Methylsulfonylethyl)-5-(o,o'-difluorophenyl)-7-chloro-1,3-dihydro-2H-1,4-benzodiazepin-2-one
1-(β-Methylsulfonylethyl)-5-(o,o'-dichlorophenyl)-7-chloro-1,3-dihydro-2H-1,4-benzodiazepin-2-one
1-(β-Methylsulfonyl)-5-(o,o'-xylyl)-7-chloro-1,3-dihydro-2H-1,4-benzodiazepin-2-one
1-(β-Methylsulfonylethyl)-5-(o-fluoro-p-chlorophenyl)-7-chloro-1,3-dihydro-2H-1,4-benzodiazepin-2-one
1-(β-Ethylsulfonyl)-5-(o,o'-difluorophenyl)-7-chloro-1,3-dihydro-2H-1,4-benzodiazepin-2-one
1-(β-Ethylsulfonylethyl)-5-(o,o'-dichlorophenyl)-7-chloro-1,3-dihydro-2H-1,4-benzodiazepin-2-one
1-(β-Ethylsulfonylethyl)-5-(o-fluoro-o'-chlorophenyl)-7-chloro-1,3-dihydro-2H-1,4-benzodiazepin-2-one
1-(β-Isopropylsulfonylethyl)-5-(o,o'-dichlorophenyl)-7-chloro-1,3-dihydro-2H-1,4-benzodiazepin-2-one
1-(β-Methylsulfonylpropyl)-5-(o,o'-dichlorophenyl)-7-chloro-1,3-dihydro-2H-1,4-benzodiazepin-2-one
1-(β-Ethylsulfonylpropyl)-5-(o,o'-difluorophenyl)-7-chloro-1,3-dihydro-2H-1,4-benzodiazepin-2-one
1-(β-Ethylsulfonylpropyl)-5-(o,o'-dichlorophenyl)-7-chloro-1,3-dihydro-2H-1,4-benzodiazepin-2-one
1-Methylsulfinylmethyl-5-(o,o'-difluorophenyl)-7-chloro-1,3-dihydro-2H-1,4-benzodiazepin-2-one
1-Methylsulfinylmethyl-5-(o,o'-dichlorophenyl)-7-chloro-1,3-dihydro-2H-1,4-benzodiazepin-2-one
1-Methylsulfinylmethyl-5-(o-fluoro-o'-chlorophenyl)-7-chloro-1,3-dihydro-2H-1,4-benzodiazepin-2-one
1-Ethylsulfinylmethyl-5-(o,o'-difluorophenyl)-7-chloro-1,3-dihydro-2H-1,4-benzodiazepin-2-one
1-Ethylsulfinylmethyl-5-(o,o'-dichlorophenyl)-7-chloro-1,3-dihydro-2H-1,4-benzodiazepin-2-one
1-(β-Methylsulfinylethyl)-5-(o,o'-difluorophenyl)-7-chloro-1,3-dihydro-2H-1,4-benzodiazepin-2-one
1-(β-Methylsulfinylethyl)-5-(o,o'-dichlorophenyl)-7-chloro-1,3-dihydro-2H-1,4-benzodiazepin-2-one
1-Ethylsulfinylmethyl-5-(o,o'-xylyl)-7-chloro-1,3-dihydro-2H-1,4-benzodiazepin-2-one
1-(β-Methylsulfinylethyl)-5-(o,o'-xylyl)-7-chloro-1,3-dihydro-2H-1,4-benzodiazepin-2-one
1-(β-Ethylsulfonylethyl)-5-(o-methyl-p-chlorophenyl)-7-chloro-1,3-dihydro-2H-1,4-benzodiazepin-2-one
1-(β-Methylsulfonylethyl)-5-(p-methyl-o-chlorophenyl)-7-chloro-1,3-dihydro-2H-1,4-benzodiazepin-2-one
1-Methylsulfinylmethyl-5-(o-methyl-p-chlorophenyl)-7-chloro-1,3-dihydro-2H-1,4-benzodiazepin-2-one
1-(β-Ethylsulfinylethyl)-5-(o,o'-difluorophenyl)-7-chloro-1,3-dihydro-2H-1,4-benzodiazepin-2-one
1-(β-Ethylsulfinylethyl)-5-(o,o'-dichlorophenyl)-7-chloro-1,3-dihydro-2H-1,4-benzodiazepin-2-one
1-(β-Methylsulfinylpropyl)-5-(o,o'-dichlorophenyl)-7-chloro-1,3-dihydro-2H-1,4-benzodiazepin-2-one
1-(β-Ethylsulfinylpropyl)-5-(o,o'-difluorophenyl)-7-chloro-1,3-dihydro-2H-1,4-benzodiazepin-2-one
1-(β-Ethylsulfinylpropyl)-5-(o,o'-dichlorophenyl)-7-chloro-1,3-dihydro-2H-1,4-benzodiazepin-2-one The thus obtained benzodiazepine derivatives of the formula (I) and (I-a) form pharmaceutically acceptable acid addition salts with pharmaceutically acceptable inorganic and organic acids such as hydrochloric acid, hydrobromic acid, sulfuric acid, phosphoric acid, nitric acid, acetic acid, maleic acid, fumaric acid, tartaric acid, succinic acid, citric acid, camphorsulfonic acid, ethanesulfonic acid, ascorbic acid, lactic acid, and the like.

The benzodiazepine derivatives of the formula (I), especially (I-a) or their pharmaceutical acceptable acid addition salts are useful as sedatives, muscle relaxant, hypnotics and anticonvulsants.

Illustratively, 1-($\beta$-methylsulfonylethyl)-5-(o-fluorophenyl)-7-chloro-1,3-dihydro-2H-1,4-benzodiazepin-2-one and 1-($\beta$-methylsulfinylethyl)-5-phenyl-7-chloro-1,3-dihydro-2H-1,4-benzodiazepin-2-one show anticonvulsant, muscle relaxant and hexobarbital potentiation activities with low toxicy. These pharmacological activities of the present compounds are found to be more potent than those of the chemical related compounds, Chlorodiazepoxide (2-methylamino-5-phenyl-7-chloro-3H-1,4-benzodiazepin-4-oxide).

Benzodiazepines or salts thereof of the present invention can be administered parenterally or orally in therapeutic dosage forms with dosage adjusted to individual needs, that is, in solid or liquid dosage forms such as tablets, dragees, capsules, suspensions, solutions, elixirs and the like.

This invention is further illustrated by the following examples of preferred embodiments thereof, which are presented for purpose of illustration and are not intended to limit the scope of the invention.

EXAMPLE 1

A solution of 1 g of 5-phenyl-7-chloro-1,3-dihydro-2H-1,4-benzodiazepin-2-one in 15 ml of N,N-dimethylformamide is added to a suspension of 0.3 g sodium methoxide in 15 ml of N,N-dimethylformamide, and the mixture is heated at 50° – 60° C for 1 hour. After the mixture is cooled, a solution of 2 ml of $\beta$-methylsulfinylethyl chloride in 10 ml of toluene is added thereto below 10° C. The resulting mixture is stirred at room temperature for 30 minutes, and then at 80° – 90° C for 5 hours. The reaction mixture is poured onto ice water, and extracted with methylene chloride. The methylene chloride extracts are combined and dried over anhydrous sodium sulfate, and the solvent is removed under reduced pressure. The residue is allowed to stand to form crystals. Recrystallization from ethyl acetate gives, 1-($\beta$-methylsulfinylethyl)-5-phenyl-7-chloro-1,3-dihydro-2H-1,4-benzodiazepin-2-one as colorless prisms, m.p. 166° – 167° C.

EXAMPLE 2

Using the procedure similar to that in Example 1, but replacing $\beta$-methylsulfinylethyl chloride by $\beta$-methylsulfonylethyl chloride, there is obtained 1-($\beta$-methylsulfonylethyl)-5-phenyl-7-chloro-1,3-dihydro-2H-1,4-benzodiazepin-2-one, m.p. 218° – 219° C.

Similarly, the following compounds are obtained.
1-Methylsulfonylmethyl-5-phenyl-7-chloro-1,3-dihydro-2H-1,4-benzodiazepin-2-one, m.p. 163° – 165° C.
1-Methylsulfonylmethyl-5-phenyl-7-nitro-1,3-dihydro-2H-1,4-benzodiazepin-2-one, m.p. 192° – 194° C.
1-Methylsulfinylmethyl-5-phenyl-7-chloro-1,3-dihydro-2H-1,4-benzodiazepin-2-one, m.p. 158° – 159° C.
1-Methylsulfinylmethyl-5-phenyl-7-nitro-1,3-dihydro-2H-1,4-benzodiazepin-2-one, m.p. 190° – 192° C.
1-($\beta$-Methylsulfonylethyl)-5-(o-fluorophenyl)-7-chloro-1,3-dihydro-2H-1,4-benzodiazepin-2-one, m.p. 155° – 156° C.

EXAMPLE 3

To a solution of 0.5 g of 2-($\beta$-methylsulfonylethyl)amino-5-chlorobenzophenone in 20 ml of dry methylene chloride is added 0.5 g of oxazolidine-2,5-dione. To the mixture is added 20 ml of ethereal hydrogen chloride under cooling. The mixture is stirred at room temperature. After completion of the reaction, the mixture is poured into ice water, basified with aqueous ammonia and extracted with methylene chloride. The extracts are combined and dried over anhydrous sodium sulfate, and the solvent is removed under reduced pressure. The residue is added with isopropyl alcohol to form crystals. Recrystallization from acetone gives 1-($\beta$-methylsulfonylethyl)-5-phenyl-7-chloro-1,3-dihydro-2H-1,4-benzodiazepin-2-one as colorless leaflets, m.p. 218° – 219° C.

EXAMPLE 4

Using the procedure similar to that in Example 3 but replacing 2-($\beta$-methylsulfonylethyl)amino-5-chlorobenzophenone by 2-($\beta$-methylsulfinylethyl)amino-5-chlorobenzophenone, there is obtained 1-($\beta$-methylsulfinylethyl)-5-phenyl-7-chloro-1,3-dihydro-2H-1,4-benzodiazepin-2-one, m.p. 166° – 167° C.

Similarly, the following compounds are obtained.
1-Methylsulfonylmethyl-5-phenyl-7-chloro-1,3-dihydro-2H-1,4-benzodiazepin-2-one, m.p. 163° – 165° C.
1-Methylsulfonylmethyl-5-phenyl-7-nitro-1,3-dihydro-2H-1,4-benzodiazepin-2-one, m.p. 192° – 194° C.
1-Methylsulfonylmethyl-5-phenyl-7-chloro-1,3-dihydro-2H-1,4-benzodiazepin-2-one, m.p. 158° – 159° C.
1-Methylsulfinylmethyl-5-phenyl-7-nitro-1,3-dihydro-2H-1,4-benzodiazepin-2-one, m.p. 190° – 192° C.
1-($\beta$-Methylsulfonylethyl)-5-(o-fluorophenyl)-7-chloro-1,3-dihydro-2H-1,4-benzodiazepin-2-one, m.p. 155° – 156° C.

EXAMPLE 5

A solution of 1 g of chromic anhydride in 1 ml of water is added to a mixture of 1 g of 1-($\beta$-methylthioethyl)-2-aminomethyl-3-phenyl-5-chloroindole and 20 ml of acetic acid. The mixture is stirred overnight at room temperature. The reaction mixture is poured into ice water, basified with ammonia water and extracted with methylene chloride. The methylene chloride extracts are combined and dried over anhydrous sodium sulfate, and the solvent is removed. The residue is dissolved in chloroform and purified by filtration through silica gel.

Crystals are obtained from the eluate of ethyl acetate. Recrystallization from acetone gives 1-($\beta$-methylsulfonylethyl)-5-phenyl-7-chloro-1,3-dihydro-2H-1,4-benzodiazepin-2-one, m.p. 218° – 219° C.

EXAMPLE 6

Using the procedure similar to that in Example 5 but replacing 1-($\beta$-methylthioethyl)-2-aminomethyl-3-phenyl-5-chloroindole by 1-($\beta$-methylthioethyl)-2-aminomethyl-3-(o-fluorophenyl)-5-chloroindole, there is obtained 1-($\beta$-methylsulfonylethyl)-5-(o-fluorophenyl)-7-chloro-1,3-dihydro-2H-1,4-benzodiazepin-2-one, m.p. 155° – 156° C.

Similarly, the following compounds are obtained.

1-Methylsulfonylmethyl-5-phenyl-7-chloro-1,3-dihydro-2H-1,4-benzodiazepin-2-one, m.p. 163° – 165° C.
1-Methylsulfonylmethyl-5-phenyl-7-nitro-1,3-dihydro-2H-1,4-benzodiazepin-2-one, m.p. 192° – 194° C.

EXAMPLE 7

Using the procedure similar to that in Example 5 but replacing 1-(β-methylthioethyl)-2-aminomethyl-3-phenyl-5-chloroindole by 1-(β-methylsulfinylethyl)-2-aminomethyl-3-phenyl-5-chloroindole, there is obtained 1-(β-methylsulfonylethyl)-5-phenyl-7-chloro-1,3-dihydro-2H-1,4-benzodiazepin-2-one, m.p. 218° – 219° C.

Similarly, the following compounds are obtained.
1-(β-Methylsulfonylethyl)-5-(o-fluorophenyl)-7-chloro-1,3-dihydro-2H-1,4-benzodiazepin-2-one, m.p. 155° – 156° C.
1-Methylsulfonylmethyl-5-phenyl-7-chloro-1,3-dihydro-2H-1,4-benzodiazepin-2-one, m.p. 163° – 165° C.
1-Methylsulfonylmethyl-5-phenyl-7-nitro-1,3-dihydro-2H-1,4-benzodiazepin-2-one, m.p. 192° – 194° C.

EXAMPLE 8

A solution of 10 ml of 15% aqueous hydrogen peroxide is added with ice-cooling to a mixture of 1.5 g of 1-(β-methylthioethyl)-5-phenyl-7-chloro-1,3-dihydro-2H-1,4-benzodiazepin-2-one and 20 ml of acetic acid. The resultant mixture is stirred at 0° C for 30 minutes and then at room temperature for 1 hour. The reaction mixture is poured into ice water, basified with ammonia water and extracted with chloroform. The chloroform extracts are combined, dried over anhydrous sodium sulfate, and the solvent is removed under reduced pressure. The residue is allowed to stand to form crystals. Recrystallization from ethylacetate gives 1-(β-methylsulfinylethyl)-5-phenyl-7-chloro-1,3-dihydro-2H-1,4-benzodiazepin-2-one, m.p. 166° – 167° C.

EXAMPLE 9

Using the procedure similar to that in Example 9, but replacing 1-(β-methylthioethyl)-5-phenyl-7-chloro-1,3-dihydro-2H-1,4-benzodiazepin-2-one by 1-(β-methylthioethyl)-5-(o-fluorophenyl)-7-chloro-1,3-dihydro-2H-1,4-benzodiazepin-2-one, there is obtained 1-(β-methylsulfonylethyl)-5-(o-fluorophenyl)-7-chloro-1,3-dihydro-2H-1,4- benzodiazepin-2-one, m.p. 155° – 156° C.

EXAMPLE 10

Using the procedure similar to that in Example 9, but replacing 1-(β-methylthioethyl)-5-phenyl-7-chloro-1,3-dihydro-2H-1,4-benzodiazepin-2-one by 1-(β-methylsulfinylethyl)-5-phenyl-7-chloro-1,3-dihydro-2H-1,4-benzodiazepin-2-one, there is obtained 1-(β-methylsulfonylethyl)-5-phenyl-7-chloro-1,3-dihydro-2H-1,4-benzodiazepin-2-one, m.p. 218° – 219° C.

Similarly, the following compound is obtained.
1-(β-Methylsulfonylethyl)-5-(o-fluorophenyl)-7-chloro-1,3-dihydro-2H-1,4-benzodiazepin-2-one, m.p. 155° – 156° C.

EXAMPLE 11

A mixture of 1 g of 2-[$N^1$-(β-methylsulfonylethyl)-$N^1$-($N^2$-carbobenzoxyglycyl)amido]-5-chlorobenzophenone and 20 ml of 30% hydrogen bromide-acetic acid is stirred at room temperature. The reaction mixture is poured into water, basified with ammonia water and extracted with methylene chloride. The methylene chloride extracts are combined and dried over anhydrous sodium sulfate, and the solvent is removed. The residue is crystallized from isopropyl alcohol to give 1-(β-methylsulfonylethyl)-5-phenyl-7-chloro-1,3-dihydro-2H-1,4-benzodiazepin-2-one, which is recrystallized from acetone, m.p. 218° – 219° C.

Similarly, using the above procedure but replacing 2-[$N^1$-(β-methylsulfonylethyl)-$N^1$-($N^2$-carbobenzoxyglycyl)amido]-5-chloro-benzophenone by 2-[$N^1$-(β-methylsulfonylethyl)-$N^1$-($N^2$-carbobenzoxyglycyl)amido]-5-chloro-2'-fluoro-benzophenone, there is obtained 1-(β-methylsulfonylethyl)-5-(o-fluorophenyl)-7-chloro-1,3-dihydro-2H-1,4-benzodiazepin-2-one, m.p. 155° – 156° C.

Similarly, the following compound is obtained.
1-(β-Methylsulfinylethyl)-5-phenyl-7-chloro-1,3-dihydro-2H-1,4-benzodiazepin-2-one, m.p. 166° – 167° C.

EXAMPLE 12

To a mixture of 1 g of 2-(N-phtalimidoacetyl-N-β-methylsulfonylethyl)amino-5-chloro-2'-fluorobenzophenone, 15 ml of methylene chloride and 15 ml of ethanol is added a solution of 2 g of hydrazine hydrate in 2 ml of water. The mixture is stirred at room temperature. The reaction mixture is concentrated under reduced pressure, diluted with water, basified with ammonia water and extracted with ether. The ethereal layers are combined and dried over anhydrous sodium sulfate and the solvent is removed. The residue is crystallized from a small amount of isopropyl ether to give 1-(β-methylsulfonylethyl)-5-(o-fluorophenyl)-7-chloro-1,3-dihydro-2H-1,4-benzodiazepin-2-one. Recrystallization from isopropylethermethylene chloride gives colorless prisms, m.p. 155° – 156° C.

Similarly, the following compounds are obtained.
1-(β-Methylsulfonylethyl)-5-phenyl-7-chloro-1,3-dihydro-2H-1,4-benzodiazepin-2-one, m.p. 218° – 219° C.
1-(β-Methylsulfinylethyl)-5-phenyl-7-chloro-1,3-dihydro-2H-1,4-benzodiazepin-2-one, m.p. 166° – 167° C.

What is claimed is:
1. 1-(β-Methylsulfinylethyl)-5-(o-fluorophenyl)-7-chloro-1,3-dihydro-2H-1,4-benzodiazepin-2-one.
2. 1-(β-Ethylsulfinylethyl)-5-(o-fluorophenyl)-7-chloro-1,3-dihydro-2H-1,4-benzodiazepin-2-one and its non-toxic, pharmaceutically acceptable acid addition salt.
3. 1-(γ-Ethylsulfonylpropyl)-5-(o-fluorophenyl)-7-chloro-1,3-dihydro-2H-1,4-benzodiazepin-2-one.

* * * * *